(12) United States Patent
Storhoff et al.

(10) Patent No.: US 7,253,277 B2
(45) Date of Patent: Aug. 7, 2007

(54) NANOPARTICLE POLYANION CONJUGATES AND METHODS OF USE THEREOF IN DETECTING ANALYTES

(75) Inventors: James J. Storhoff, Evanston, IL (US); Robert L. Letsinger, Bloomington, IN (US); Susan R. Hagenow, Salem, WI (US)

(73) Assignee: Nanosphere, Inc., Northbrook, IL (US)

( * ) Notice: Subject to any disclaimer, the term of this patent is extended or adjusted under 35 U.S.C. 154(b) by 564 days.

(21) Appl. No.: 10/612,422

(22) Filed: Jul. 2, 2003

(65) Prior Publication Data

US 2004/0053222 A1    Mar. 18, 2004

Related U.S. Application Data

(60) Provisional application No. 60/393,255, filed on Jul. 2, 2002.

(51) Int. Cl.
| | |
|---|---|
| C07H 19/04 | (2006.01) |
| C07K 16/00 | (2006.01) |
| C12Q 1/68 | (2006.01) |
| C12Q 1/00 | (2006.01) |
| C07H 21/02 | (2006.01) |

(52) U.S. Cl. .................. 536/26.6; 536/23.1; 530/300; 435/4; 435/5; 435/6; 977/702

(58) Field of Classification Search ........... 977/702; 536/23.1, 26.6; 530/300; 435/4, 5, 6
See application file for complete search history.

(56) References Cited

U.S. PATENT DOCUMENTS

| | | | |
|---|---|---|---|
| 4,193,983 A | 3/1980 | Ullman et al. | |
| 4,256,834 A | 3/1981 | Zuk et al. | |
| 4,261,968 A | 4/1981 | Ullman et al. | |
| 4,313,734 A | 2/1982 | Leuvering | |
| 4,318,707 A | 3/1982 | Litman et al. | |
| 4,650,770 A | 3/1987 | Liu et al. | |
| 4,713,348 A | 12/1987 | Ullman | |
| 4,853,335 A | 8/1989 | Olsen et al. | |
| 4,868,104 A | 9/1989 | Kurn et al. | |
| 4,996,143 A | 2/1991 | Heller et al. | |
| 5,225,064 A | 7/1993 | Henkens et al. | |
| 5,284,748 A | 2/1994 | Mroczkowski et al. | |
| 5,288,609 A | 2/1994 | Engelhardt et al. | |
| 5,294,369 A | 3/1994 | Shigekawa et al. | |
| 5,360,895 A | 11/1994 | Hainfeld et al. | |
| 5,384,073 A | 1/1995 | Shigekawa et al. | |
| 5,384,265 A | 1/1995 | Kidwell et al. | |
| 5,460,831 A | 10/1995 | Kossovsky et al. | |
| 5,472,881 A | 12/1995 | Beebe et al. | |
| 5,508,164 A | 4/1996 | Kausch et al. ................. 435/6 |
| 5,514,602 A | 5/1996 | Brooks, Jr. et al. | |
| 5,521,289 A | 5/1996 | Hainfeld et al. | |
| 5,543,158 A | 8/1996 | Gref et al. | |
| 5,571,726 A | 11/1996 | Brooks, Jr. et al. | |
| 5,599,668 A | 2/1997 | Stimpson et al. | |
| 5,609,907 A | 3/1997 | Natan | |
| 5,637,508 A | 6/1997 | Kidwell et al. | |
| 5,665,582 A | 9/1997 | Kausch et al. | |
| 5,681,943 A | 10/1997 | Letsinger et al. | |
| 5,751,018 A | 5/1998 | Alivisatos et al. | |
| 5,830,986 A | 11/1998 | Merrill et al. | |
| 5,900,481 A | 5/1999 | Lough et al. ............... 536/55.3 |
| 5,922,537 A | 7/1999 | Ewart et al. ................... 435/6 |
| 5,939,021 A | 8/1999 | Hansen et al. | |
| 5,972,615 A | 10/1999 | An et al. ........................ 435/6 |
| 5,990,479 A | 11/1999 | Weiss et al. | |
| 6,025,202 A | 2/2000 | Natan | |
| 6,149,868 A | 11/2000 | Natan et al. | |
| 6,203,989 B1 | 3/2001 | Goldberg et al. ............... 435/6 |
| 6,214,560 B1 | 4/2001 | Yguerabide et al. | |
| 6,251,303 B1 | 6/2001 | Bawendi et al. | |
| 6,264,825 B1 | 7/2001 | Blackburn et al. ........ 205/777.5 |
| 6,277,489 B1 | 8/2001 | Abbott et al. | |
| 6,306,610 B1 | 10/2001 | Bawendi et al. | |

(Continued)

FOREIGN PATENT DOCUMENTS

EP    0 630 974 A2    6/1994

(Continued)

OTHER PUBLICATIONS

Otsuka, Hidenori, et al, "Quantitative and Reversible Lectin-Induced Association of Gold Nanoparticles Modified with a-Lactosyl-w-mercapto-poly(ethylene glycol)," *Journal of the American Chemical Society*, vol. 123, p. 8226-8230 (2001).

(Continued)

*Primary Examiner*—Jezia Riley
(74) *Attorney, Agent, or Firm*—Gregory T. Pletta (57) ABSTRACT

This invention provides polyanionic polymer conjugates containing non-nucleotide polyanionic polymers that are useful in detecting target analytes such as proteins or small molecules. The invention also provides nanoparticles bound to polyanionic polymer conjugates and methods of preparation and use thereof. The polyanionic polymer conjugates have the formula:

$$L-O-[PO_2-O-Z-O]_n-PO_2-O-X$$

wherein n ranges from 1 to 200; L represents a moiety comprising a functional group for attaching the polyanion polymer to the nanoparticle surface; Z represents a bridging group, and X represents Q, X' or -Q-X', wherein Q represents a functional group for attaching a recognition probe to the polyanion polymer, and X' represents a recognition probe.

15 Claims, 6 Drawing Sheets

U.S. PATENT DOCUMENTS

| | | | |
|---|---|---|---|
| 6,361,944 B1 | 3/2002 | Mirkin et al. | |
| 6,365,418 B1 | 4/2002 | Wagner et al. | |
| 6,417,340 B1 | 7/2002 | Mirkin et al. | 536/23.1 |
| 6,495,324 B1 | 12/2002 | Mirkin et al. | 435/6 |
| 6,506,564 B1 | 1/2003 | Mirkin et al. | |
| 6,582,921 B2 | 6/2003 | Mirkin et al. | 435/6 |
| 6,602,669 B2 | 8/2003 | Letsinger et al. | 435/6 |
| 6,610,491 B2 | 8/2003 | Mirkin et al. | 435/6 |
| 6,645,721 B2 | 11/2003 | Mirkin et al. | 435/6 |
| 6,673,548 B2 | 1/2004 | Mirkin et al. | 435/6 |
| 6,677,122 B2 | 1/2004 | Mirkin et al. | 435/6 |
| 6,682,895 B2 | 1/2004 | Mirkin et al. | 435/6 |
| 6,709,825 B2 | 3/2004 | Mirkin et al. | 435/6 |
| 6,720,147 B2 | 4/2004 | Mirkin et al. | 435/6 |
| 6,720,411 B2 | 4/2004 | Mirkin et al. | 546/23.1 |
| 6,726,847 B2 | 4/2004 | Mirkin et al. | 216/90 |
| 6,730,269 B2 | 5/2004 | Mirkin et al. | 422/68.1 |
| 6,740,491 B2 | 5/2004 | Mirkin et al. | 435/6 |
| 6,750,016 B2 | 6/2004 | Mirkin et al. | 435/6 |
| 6,759,199 B2 | 7/2004 | Mirkin et al. | 435/6 |
| 6,767,702 B2 | 7/2004 | Mirkin et al. | 435/6 |
| 6,773,884 B2 | 8/2004 | Mirkin et al. | 435/6 |
| 6,777,186 B2 | 8/2004 | Mirkin et al. | 435/6 |
| 2002/0137070 A1 | 9/2002 | Mirkin et al. | 435/6 |
| 2002/0155461 A1 | 10/2002 | Mirkin et al. | 435/6 |
| 2002/0160381 A1 | 10/2002 | Mirkin et al. | 435/6 |
| 2002/0177143 A1 | 11/2002 | Mirkin et al. | 435/6 |
| 2002/0192687 A1 | 12/2002 | Mirkin et al. | 435/6 |
| 2003/0054358 A1 | 3/2003 | Mirkin et al. | 435/6 |
| 2003/0068622 A1 | 4/2003 | Mirkin et al. | 435/6 |
| 2003/0068638 A1 | 4/2003 | Mirkin et al. | 435/6 |
| 2003/0087242 A1 | 5/2003 | Mirkin et al. | 435/6 |
| 2003/0113740 A1 | 6/2003 | Mirkin et al. | 435/6 |
| 2003/0124528 A1 | 7/2003 | Mirkin et al. | 435/6 |
| 2003/0129608 A1 | 7/2003 | Mirkin et al. | 435/6 |
| 2003/0143538 A1 | 7/2003 | Mirkin et al. | 435/6 |
| 2003/0143598 A1 | 7/2003 | Mirkin et al. | 435/6 |
| 2003/0148282 A1 | 8/2003 | Mirkin et al. | 435/6 |
| 2003/0207296 A1 | 11/2003 | Mirkin et al. | 435/6 |
| 2003/0211488 A1 | 11/2003 | Mirkin et al. | 435/6 |
| 2004/0038255 A1 | 2/2004 | Mirkin et al. | 435/6 |
| 2004/0053222 A1 | 3/2004 | Mirkin et al. | 435/6 |
| 2004/0072231 A1 | 4/2004 | Mirkin et al. | 435/6 |
| 2004/0086897 A1 | 5/2004 | Mirkin et al. | 435/6 |
| 2004/0101889 A1 | 5/2004 | Mirkin et al. | 435/6 |

FOREIGN PATENT DOCUMENTS

| | | |
|---|---|---|
| EP | 0 667 398 A2 | 8/1995 |
| WO | WO 89/06801 | 7/1989 |
| WO | WO 90/02205 | 3/1990 |
| WO | WO 92/04469 | 3/1992 |
| WO | WO 92/04469 | 5/1992 |
| WO | WO 93/10564 | 5/1993 |
| WO | WO 93/25709 | 12/1993 |
| WO | WO 94/29484 | 12/1994 |
| WO | WO 99/23258 | 12/1994 |
| WO | WO 97/40181 | 10/1997 |
| WO | WO 98/04740 | 2/1998 |
| WO | WO 98/04740 A1 | 2/1998 |
| WO | WO 98/10289 | 3/1998 |
| WO | WO 98/17317 | 4/1998 |
| WO | WO 98/21587 | 5/1998 |
| WO | WO 99/20789 | 4/1999 |
| WO | WO 99/21934 | 5/1999 |
| WO | WO 99/23258 | 5/1999 |
| WO | WO 90/54509 | 10/1999 |
| WO | WO 99/60169 | 11/1999 |
| WO | WO 00/25136 | 5/2000 |
| WO | WO 00/33079 A1 | 6/2000 |
| WO | WO 01/00876 | 1/2001 |
| WO | WO 01/00876 A1 | 1/2001 |
| WO | WO 01/51665 | 7/2001 |
| WO | WO 01/051665 A2 | 7/2001 |
| WO | WO 01/73123 | 10/2001 |
| WO | WO 01/073123 A3 | 10/2001 |
| WO | WO 01/86301 | 11/2001 |
| WO | WO 01/86301 A1 | 11/2001 |
| WO | WO 02/04681 | 1/2002 |
| WO | WO 02/004681 A3 | 1/2002 |
| WO | WO 02/18643 | 3/2002 |
| WO | WO 02/018643 A3 | 3/2002 |
| WO | WO 02/36169 | 5/2002 |
| WO | WO 00/33079 | 6/2002 |
| WO | WO 02/46472 | 6/2002 |
| WO | WO 02/046472 A3 | 6/2002 |
| WO | WO 02/46483 | 6/2002 |
| WO | WO 02/079490 A3 | 10/2002 |
| WO | WO 02/096262 A2 | 12/2002 |
| WO | WO 03/008539 A3 | 1/2003 |
| WO | WO 03/035829 A3 | 5/2003 |
| WO | WO 03/081202 A3 | 10/2003 |
| WO | WO 03/087188 A1 | 10/2003 |
| WO | WO 03/095973 A2 | 11/2003 |
| WO | WO 2004/004647 A3 | 1/2004 |
| WO | WO 2004/053105 A2 | 6/2004 |

OTHER PUBLICATIONS

Ahmadi, T.S. et al., *Science*, 272, 1924 (1996).
Bahnemann, in *Photochemical Conversion and Storage of Solar Energy* (eds. Pelizetti and Schiavello 1991), p. 251.
Bassell, et al., *J. Cell Biol.*, 126, 863-876 (1994).
Bottomley et al., J. Vac. Sci. Technol. A, 10, 591 (1992).
Braun et al., *Nature*, 391, 775 (1998).
Braun-Howland et al., *Biotechniques*, 13, 928-931 (1992).
Brousseau et al., J. Am. Chem. Soc., 120: 7645 (1998).
Brus, *Appl. Phys. A.*, 53, 465 (1991).
Burwell, *Chemical Technology*, 4, 370-377 (1974).
Chrisey et al., Nucleic Acids Res., 24, 3031-3039 (1996).
Chrisey et al., Nucleic Acids Res., 24, 3040-3047 (1996).
Curtis, A.C., et al., *Angew. Chem. Int. Ed. Engl.*, 27, 1530 (1988).
Elghanian et al., Science, 277: 1078 (1997).
Freeman et al., Science, 267: 1629 (1995).
D. I. Gittins, F. Caruso, *J. Phys. Chem. B* 105, 6846-6852 (2001).
Grabar et al., *Anal. Chem.*, 67, 735-743 (1995).
Hegner et al., FEBS Lett., 336, 452 (1993).
Henglein, *Chem. Rev.*, 89, 1861 (1989).
Henglein, A. et al., *J. Phys. Chem.*, 99, 14129 (1995).
Henglein, *Top. Curr. Chem.*, 143, 113 (1988).
Letsinger, R. L.; Elghanian, R.; Viswanadham, G.; Mirkin, C. A. *Bioconjugate Chemistry* 2000, 11, 289-291.
Massart, R., *IEEE Taransactions On Magnetics*, 17, 1247 (1981).
Matteucci and Caruthers, *J. Am. Chem. Soc.*, 103, 3185-3191 (1981).
Mirkin et al., Nature, 382: 607 (1996).
Mirkin et al., U.S. Appl. No. 09/927,777, filed Aug. 10, 2001.
Mirkin et al., U.S. Appl. No. 09/760,500, filed Jan. 12, 2001.
Mirkin et al., U.S. Appl. No. 09/344,667, filed Jun. 25, 1999.
Mirkin et al., U.S. Appl. No. 09/603,830, filed Jun. 26, 2000.
Mirkin et al., PCT Patent Application No. PCT/US97/12783, filed Jul. 21, 1997.
Mirkin et al., PCT Patent Application No. PCT/US00/17507, filed Jun. 26, 2000.
Mirkin et al., PCT Patent Application No. PCT/US01/01190, filed Jan. 12, 2001.
Mirkin et al., U.S. Appl. No. 09/820,279, filed Mar. 28, 2001.
Mirkin et al., PCT Patent Application No. PCT/US01/10071, filed Mar. 28, 2001.
Mucic et al., Chem. Commun., 555 (1996).
Olshavsky et al., *J. Am. Chem. Soc.*, 112, 9438 (1990).
Storhoff et al., J. Clust. Sci., 8: 179 (1997).
Storhoff et al., J. Am. Chem. Soc., 120: 1959 (1998).
Uchida et al., *J. Phys. Chem.*, 95, 5382 (1991).

Wang and Herron, *J. Phys. Chem.*, 95, 525 (1991).
Weller, *Angew. Chem. Int. Ed. Engl.*, 32, 41 (1993).
Zhu et al., *J. Am. Chem. Soc.*, 119: 235 (1997).
Zimmermann and Cox, Nucleic Acids Res., 22, 492 (1994).
Letsinger, R., et al., "Chemistry of Oligonucleotide-Gold Nanoparticle Conjugates," *Phosphorus, Sulfur and Silcon*, vol. 144, p. 359-362 (1999).
Letsinger, R., et al., "Use of a Steroid Cyclic Disulfide Anchor in Constructing Gold Nanoparticle—Oligonucleotide Conjugates," *Bioconjugate Chem*, p. 289-291 (2000).
Li Z., et al., "Multiple thiol-anchor capped DNA-gold nanoparticle conjugates," *Nucleic Acids Research*, vol. 30, p. 1558-1562 (2002).
Nuzzo R., et al., "Spontaneously Organized Molecular Assemblies. 3. Preparation and Properties of Solution Adsorbed Monolayers of Organic Disulfides on Gold Surfaces," *J. Am Chem. Soc.*, vol. 109, p. 2358-2368 (1987).
Otsuka, H., et al., "Quantitative and Reversible Lectin-Induced Association of Gold Nonoparticles Modified with []-Lactosyl-[]-mercapto-poly(ethyleneglycol)," *J. Am Chem. Soc.*, vol. 123, p. 8226-8230 (2001).
Wuelfing, P., et al., "Nanometer Gold Clusters Protected by Surface-Bound Monolayers of Thiolated Poly(ethylene glycol) Polymer Electrolyte," *J. Am Chem. Soc.*, vol. 120, p. 12696-12697 (1998).
Brada, et al., "Golden Blot"—Detection of Polyclonal and Monoclonal Antibodies Bound to Antigens on Nitrocellulose by Protein A-Gold Complexes, *Analytical Biochemistry*, vol. 42, pp. 79-83 (1984) U.S.
Dunn, et al., A Novel Method to Map Transcripts: Evidence for homology between an Adenovirus mRNA and Discrete Multiple Regions of the Viral Genome, *Cell*, vol. 12, pp. 23-36, (1997) U.S.
Hacker, High performance Nanogold—Silver in situ hybridisation, *Eur. J. Histochem*, vol. 42, pp. 111-120 (1998) U.S.
Ranki, et al., "Sandwich hybridization as a covenient method for the detection of nucleic acids in crude samples," *Gene*, vol. 21, pp. 77-85 (1983) U.S.
Romano, et al., "An antiglobulin reagent labelled with colloidal gold for use in electron microscopy," *Immunochemistry*, vol. 11, pp. 521-522 (1974) Great Britain.
Alivisatos et al., "Organization of 'nanocrystal molecules' using DNA," *Nature*, vol. 382, pp. 609-611 (1996).
Bain, et al., "Modeling Organic Surfaces with Self-Assembled Monolayers," *Angew. Chem. Int. Ed. Engl.*, vol. 28, pp. 506-512 (1989).
Bradley, "The Chemistry of Transition Metal Colloids," *Clusters and Colloids: From Theory to Applications*, G. Schmid, Editor, BCH, Weinheim, New York, pp. 459-542 (1994).
Brust et al., "Novel Gold-Dithiol Nano-Networks with Non-Metallic Electronic Properties," *Adv. Mater.*, vol. 7, pp. 795-797 (1995).
Chen et al., "A Specific Quadrilateral Synthesized from DNA Branched Junctions," *J. Am. Chem. Soc.*, vol. 111, pp. 6402-6407 (1989).
Chen & Seeman, "Synthesis from DNA of a molecule with the connectivity of a cube," *Nature*, vol. 350, pp. 631-633 (1991).
Chen et al., Crystal Structure of a Four-Stranded Intercalated DNA: d(C$_4$)$^‡$*Biochem.*, vol. 33, pp. 13540-13546 (1994).
Dagani, "Supramolecular Assemblies DNA to organize gold nanoparticles," *Chemical & Engineering News*, p. 6-7, Aug. 19, 1996.
Dubois & Nuzzo, "Synthesis, Structure, and Properties of Model Organic Surfaces," *Annu. Rev. Phys. Chem.*, vol. 43, pp. 437-464 (1992).
Elghanian et al., "Selective Colorimetric Detection of Polynucleotides Based on the Distance-Dependent Optical Properties of Gold Nanoparticles," *Science*, vol. 277, pp. 1078-1081 (1997).
Grabar et al., "Preparation and Characterization of Au Colloid Monolayers," *Anal. Chem.* vol. 67, pp. 735-743 (1995).
Hacia et al., "Detection heterozygous mutations in BRCA1 using high density oligonucleotide arrays and two-colour fluorescence analysis," *Nature Genet.*, vol. 14, pp. 441-447 (1996).
Jacoby, "Nanoparticles change color on binding to nucleotide target," *Chemical &Engineering News*, p. 10, Aug. 25, 1997.

Letsinger et al., Use of Hydrophobic Substituents in Controlling Self-Assembly of Oligonucleotides, *J. Am. Chem. Soc.*, vol. 115, pp. 7535-7536 (1993).
Letsinger et al., "Control of Excimer Emission and Photochemistry of Stilbene Units by Oligonucleotide Hybridization," *J. Am. Chem. Soc.*, vol. 116, pp. 811-812 (1994).
Marsh et al., "A new DNA nanostructure, the G-wire, imaged by scanning probe microscopy," *Nucleic Acids Res.*, vol. 23, pp. 696-700 (1995).
Mirkin, "H-DNA and Related Structures," *Annu. Review Biophys. Biomol. Struct.*, vol. 23, pp. 541-576 (1994).
Mirkin et al., "A DNA-based method for ratinally assembling nanoparticles into macroscopic materials," *Nature*, vol. 382, pp. 607-609 (1996).
Mirkin et al., "DNA-Induced Assembly of Gold Nanoparticles: A Method for Rationally Organizing Colloidal Particles into Ordered Macroscopic Materials," *Abstract* 249, Abstracts of Papers Part 1, 212 ACS National Meeting 0-8412-3402-7, American Chemical Society, Orlando, FL, Aug. 25-29, 1996.
Mucic et al., "Synthesis and characterizations of DNA with ferrocenyl groups attached to their 5'-termini: electrochemical characterization of a redox-active nucleotide monolayer," *Chem. Commun.*, pp. 555-557 (1996).
Mulvaney, "Surface Plasmon Spectroscopy of Nanosized Metal Particles," *Langmuir*, vol. 12, pp. 788-800 (1996).
Rabke-Clemmer et al., "Analysis of Functionalized DNA Adsorption on Au(111) Using Electron Spectroscopy," *Langmuir*, vol. 10, pp. 1796-1800 (1994).
Roubi, "Molecular Machines—Nanodevice with rotating arms assembled from synthetic DNA," *Chemical & Engineering News*, p. 13, (Jan. 1999).
Seeman et al., "Synthetic DNA knots and catenanes," *New J. Chem.*, vol. 17, pp. 739-755 (1993).
Shaw & Wang, "Knotting of a DNA Chain During Ring Closure," *Science*, vol. 260, pp. 533-536 (1993).
Shekhtman et al., "Sterostructure of replicative DNA catenanes from eukaryotic cells," *New J. Chem.* vol. 17, pp. 757-763 (1993).
Smith and Feigon, "Quadruplex structure of Oxytricha telomeric DNA oligonucleotides," *Nature*, vol. 356, pp. 164-168 (1992).
Thein et al., "The use of synthetic oligonucleotides as specific hybridization probes in the diagnosis of genetic disorders," 2nd Ed., K.E. Davies, Ed., Oxford University Press, New York, Tokyo, p. 21-33 (1993).
Wang et al., "Assembly and Characterization of Five-Arm and Six-Arm DNA Branched Junctions," *Biochem.*, vol. 30, pp. 5667-5674 (1991).
Wang et al., "A DNA Aptamer Which Binds to and Inhibits Thrombin Exhibits a New Structural Motif for DNA," *Biochem.*, vol. 32, pp. 1899-1904 (1993).
Weisbecker et al., "Molecular Self-Assembly of Aliphatic Thiols on Gold Colloids," *Langmuir*, vol. 12, pp. 3763-3772 (1996).
Wells, "Unusual DNA Structures," *J. Biol. Chem.*, vol. 263, pp. 1095-1098 (1988).
Zhang et al., "Informational Liposomes: Complexes Derived from Cholesteryl-conjugated Oligonucleotides and Liposomes," *Tetrahedron Lett.*, vol. 37, pp. 6243-6246 (1996).
O.D. Velev, et al., "In Situ Assembly of Collordal Particles into Miniaturized Biosensors," *Langmuir*, vol. 15, No. 11, pp. 3693-3698, May 25, 1999.
Stimpson, et al., "Real-time detection of DNA hybridization and melting on oligonucleotide arrays by using optical wave guides," *Proc. Natl. Acad. Sci..*, vol. 92, pp. 6379-6383, California Institute of Technology (1995) U.S.
Storhoff, et al., "Strategies for Organizing Nanoparticles into Aggregate Structures and Functional Materials," *Journal of Cluster Science*, vol. 8, No. 2, pp. 179-217, Plenum Publishing Corporation (1997) U.S.
Storhoff, et al., "One-Pot Colorimetric Differentiation of Polynucleotides with Single Base Imperfections Using Gold Nanoparticle Probes," *J. Am. Chem. Soc.*, vol. 20, pp. 1961-1964, American Chemical Society (1998) U.S.

Tomlinson, et al., "Detection of Biotinylated Nucleic Acid Hybrids by Antibody-Coated Gold Colloid," *Analytical Biochemistry,* vol. 171, pp. 217-222, (1988).

Velev, et al., "In Situ Assembly of Colloidal Particles into Miniaturized Biosensors," *Langmuir,* vol. 15, No. 11, pp. 3693-3698, American Chemical Society (1999) U.S.

Zhu, et al., "The First Raman Spectrum of an Organic Monolayer on a High-Temperature Superconductor: Direct Spectroscopic Evidence for a Chemical Interaction between an Amine and $Yba_2Cu_3O_{7-\delta}$," *J. Am. Chem. Soc.,* vol. 119, pp. 235-236, American Chemical Society (1997) U.S.

Yguerabide, et al., "Light-Scattering Submicroscopic Particles as Highly Fluorescent Analogs and Their Use as Tracer Labels in Clinical and Biological Applications," I. Theory, *Analytical Biochemistry,* vol. 262, pp. 137-156 (1998) U.S.

Yguerabide, et al., "Light-Scattering Submicroscopic Particles as Highly Fluorescent Analogs and Their Use as Tracer Labels in Clinical and Biological Applications," II. Experimental Characterization, *Analytical Biochemistry,* vol. 262, pp. 157-176 (1998) U.S.

Mohanty J., et al. "Pulsed laser excitation of phosphate stabilized silver nanoparticles," *Proc. Indian Acd. Sci.,* vol. 112, No. 1, p. 63-72.

Nicewarner—Peña S., et al., "Hybridization and Enzymatic Extension of Au Nanoparticle-Bound Oligonucleotides," *J. Am. Chem. Soc.,* vol. 124, p. 7314-7323 (2002).

Whitesides G.M., et al., "Soft Lithography in Biology and Biochemistry," *Annu. Rev. Biomed. Eng.,* p. 335-373 (2001).

Shchepinov et al., "Oligonucleotide Dendrimers: Synthesis And Use As Polylabelled DNA Probes", Nucleic Acids Research, 1997, vol. 25, No. 22, pp. 4447-4454.

Borman, *Chem.Eng. News,* Dec. 9, 1996, pp. 42-43 (1996).

Tomlinson et al., *Anal. Biochem,* vol. 171, pp. 217-222 (1998).

NANOPARTICLE POLYANION CONJUGATES AND METHODS OF USE THEREOF IN DETECTING ANALYTES

RELATED APPLICATIONS

This application claims the benefit of priority from U.S. provisional application No. 60/393,255, filed Jul. 2, 2002, the contents of which are incorporated herein by reference in their entirety.

FIELD OF INVENTION

This invention relates to polyanionic polymer conjugates containing non-nucleotide polyanionic polymers ("polyanions"), nanoparticles bound to polyanionic polymer conjugates and methods of preparation and use thereof in detecting target analytes such as proteins or small molecules.

BACKGROUND OF THE INVENTION

The binding of polyelectrolytes to gold nanoparticles for stabilization has been described (1). When mixing a polyelectrolyte solution with gold nanoparticles, the polymer composition, length, concentration, and total salt concentration all influence the coating of particles with polyelectrolytes (2). More specifically, high salt concentrations (0.05-0.1 M NaCl) have been found to cause aggregation of gold nanoparticles stabilized with polyelectrolytes (1, 2). This represents a significant limitation to coating nanoparticles with polyelectrolytes (2), and also severely limits the utility of polyanion coating technology since many applications such as biomolecule sensing require stability to electrolytes as well as temperature. For example, nucleic acid detection is typically performed in buffers that contain salt which promote nucleic acid hybridization, and biological fluids (e.g. urine) also contain elevated electrolyte concentrations which would destabilize polyelectrolyte nanoparticle complexes. Accordingly, a method for binding polyelectrolytes to nanoparticles that provides conjugates that are stable to electrolytes as well as temperature, conditions which are typically found in applications such as biomolecule sensing, would be highly desirable.

SUMMARY OF THE INVENTION

Herein we describe a method for preparing highly stable polyanion nanoparticle conjugates which utilizes a polyanion modified with a functional group to covalently attach the polyanion to the nanoparticle surface. This method creates a high density of polyanion moieties on the nanoparticle surface, providing highly stable polyanion-nanoparticle conjugates that may be used in biosensing applications.

This method differs from previous methods that utilize phosphate based nucleic acid moieties (3), which may produce unacceptable background in biosensing applications, as it is well known in the art that nucleic acids can bind to other nucleic acids, proteins, and small molecules. In the invention, the sugar and base moieties that constitute the nucleic acid have been removed, thus reducing or eliminating background in biosensing applications. This method also differs from previous strategies that utilize a monolayer of mercaptoundecanoic acid to anchor polyelectrolyte moieties through electrostatic attraction to the gold nanoparticle surface using a complicated layer-by-layer assembly technique (2). In the method described herein, the group responsible for binding to the nanoparticle surface is directly attached to the polyanion of interest for binding and the resulting conjugate may be immobilized on the particle in a single step. In addition, any ligand that may be used for biomolecule recognition may be attached to the polymer before or after nanoparticle modification.

The present invention provides polyanionic polymer conjugates containing non-nucleotide polyanions, nanoparticles bound with polyanionic polymer conjugates and methods for the synthesis of nanoparticles having polyanionic polymer conjugates attached thereto, and methods for detecting target analytes. The polyanions can be any water-soluble and water stable polymer or co-polymer with a net negative charge and at least one functional group that is able to bind to the nanoparticle surface.

More specifically, the invention provides polyanionic polymer conjugates containing non-nucleotide polyanions, nanoparticles and methods for covalent attachment of polyanionic polymers that serve either as "spacer" molecules between the surface of the nanoparticle and the recognition moiety, e.g., a recognition oligonucleotide probe, or as "filler" molecules that cover the surface of the nanoparticle between the oligonucleotide probes. These "spacer" and "filler" arrangements can allow for more efficient binding between the nanoparticle probe and biomolecule of interest. These nanoparticle probes comprising polyanionic polymers and a recognition element are useful for biomolecule detection (e.g. nucleic acid sequence or protein), detecting protein-ligand interactions, separation of a target oligonucleotide sequence from a population of sequences, or other methods as described previously for instance in PCT/US01/10071, filed Mar. 28, 2001 and U.S. Pat. No. 6,361,944, issued Mar. 26, 2002, which are incorporated by reference in their entirety.

Incorporation of the polyanionic polymers into the nanoparticle probes increases the stability of the nanoparticles in solution, especially colloidal gold nanoparticles in high salt solutions. The use of non-nucleic acid polyanion polymers in preparing nanoparticle conjugates is advantageous for nucleic acid and protein detection because non-specific binding interference between analytes and nanoparticle conjugate probes can be reduced.

In one embodiment, the invention provides polyanionic polymer conjugates.

In another embodiment, the invention provides nanoparticles having polyanionic polymer conjugates attached thereto.

In another embodiment, the invention provides synthetic methods for the manufacture of nanoparticle probes comprising a plurality of polyanionic polymer conjugates. The polyanionic polymer conjugates may be functionalized to attach ligands or biomolecules of interest.

In another embodiment, the invention provides for methods of synthesizing nanoparticle probes having polyanionic polymers serving as spacer, or linking, molecules between the surface of the nanoparticle and oligonucleotide probe sequences.

In another embodiment, the invention provides for methods of synthesizing nanoparticle probes having polyanionic polymers serving as spacer, or linking, molecules between the surface of the nanoparticle and small molecule ligands for detecting or binding biomolecules.

In another embodiment, the invention provides for methods of synthesizing nanoparticle probes having polyanionic polymers serving as spacer, or linking, molecules between the surface of the nanoparticle and proteins for detecting or binding biomolecules.

In another embodiment, the invention provides for methods of synthesizing nanoparticle probes having polyanionic polymers serving as spacer, or linking, molecules between the surface of the nanoparticle and oligonucleotides for detecting or binding biomolecules.

In another embodiment, the invention provides for methods of synthesizing nanoparticle probes having polyanionic polymers serving as spacer, or linking, molecules between the surface of the nanoparticle and carbohydrates for detecting or binding biomolecules.

In another embodiment, the invention provides for methods of synthesizing nanoparticle probes having polyanionic polymers serving as filler molecules on the surface of the nanoparticle, between the probes (e.g. oligonucleotide, protein, etc.) that are also attached to the surface of the nanoparticle.

In a further embodiment, the invention provides for methods of synthesizing nanoparticle probes having polyanionic polymers serving both as filler and spacer molecules.

These and other embodiments of the invention will become apparent in light of the detailed description below.

DETAILED DESCRIPTION OF THE INVENTION

The present invention is based on the discovery that non-nucleotide polyanions may be used to stabilize gold nanoparticles. Thus in one embodiment, the invention provides polyanionic polymer conjugates containing non-nucleotide polyanions. The polyanionic polymer conjugates containing non-nucleotide polyanions can be attached to nanoparticles to form nanoparticle probes useful for detecting analytes. The polyanionic polymer conjugates have the formula:

wherein n ranges from 1 to 200; L represents a moiety comprising a functional group for attaching the polyanion polymer to the nanoparticle surface; Z represents a bridging group, and X represents Q, X' or -Q-X', wherein Q represents a functional group for attaching a recognition probe to the polyanion polymer, and X' represents a recognition probe.

As indicated above, L is a moiety comprising a functional group for attaching the polyanionic polymer conjugate to the nanoparticle surface. Examples of suitable functional groups include alkanethiol groups, phosphorothioate groups (see, e.g., U.S. Pat. No. 5,472,881), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoaklylsiloxanes).

The moiety L may also comprise polyfunctional groups such as cyclic disulfide group, or polythiols or polymers with multiple functional groups that can bind to nanoparticles. The cyclic disulfides preferably have 5 or 6 atoms in their rings, including the two sulfur atoms. Suitable cyclic disulfides are available commercially or may be synthesized by known procedures. The reduced form of the cyclic disulfides can also be used. Preferably, a hydrocarbon moiety is attached to the cyclic disulfide. Suitable hydrocarbons are available commercially, and are attached to the cyclic disulfides. Preferably the hydrocarbon moiety is a steroid residue. The two sulfur atoms of the cyclic disulfide should preferably be close enough together so that both of the sulfur atoms can attach simultaneously to the nanoparticle. Most preferably, the two sulfur atoms are adjacent to each other. Examples of cyclic disulfides and polythiols are described in U.S. patent application Ser. No. 09/760,500, filed Jan. 12, 2001, and International Application Number PCT/US01/01190, filed Jan. 12, 2001, which are incorporated hererin by reference in their entirety.

As indicated above, Z is a bridging group. As a bridge, Z can be any desired chemical group. For instance, Z can be a polymer (e.g., polyethylene glycol, polymethylene), —$C_1$-$C_{10}$-alkyl-, —COO—, —$CH_2(CH_2)_v$COO—, —OCO—, $R^1N(CH_2)_v$—$NR^1$—, —$^1(CH_2)_v$-$OC(CH_2)_v$—, —$(CH_2)_v$—, —O—$(CH_2)_v$—O—, —RN—$(CH_2)_v$—, v is 0-30 and $R^1$ is H or is $G(CH_2)_v$, wherein G is —$CH_3$, —$CHCH_3$, —COOH, —$CO_2(CH_2)_vCH_3$, —OH, or —$CH_2OH$. Preferably, Z is polyethylene glycol.

X' represents a recognition probe. By "recognition probe" is meant a molecule containing at least one binding moiety with a binding affinity for a target analyte. Examples of a recognition probe suitable for use in the invention include, without limitation, a receptor, a nucleotide, a nucleoside, a polynucleotide, an oligonucleotide, double stranded DNA, an antibody, a sugar, a hapten, a protein, a peptide, a nucleic acid, a peptide nucleic acid, an amino acid, a linked nucleic acid, a nucleoside triphosphate, a carbohydrate, a lipid, a lipid bound protein, an aptamer, a virus, a cell fragment, or a whole cell.

Q, when present, represents a functional group for attaching the recognition probe to the polyanionic polymer conjugate, and can be, for example, a nucleophile that is naturally present or chemically added to the polyanion polymer or the recognition probe, such as an amino group, sulfhydryl group, hydroxy group, carboxylate group, or any suitable moiety. Q may represent —NH, —S—, —O—, or —OOC—.

Nanoparticles useful in the practice of the invention include metal (e.g., gold, silver, copper and platinum), metal oxides (e.g., $TiO_2$), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm. The nanoparticles may also be rods.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Taransactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988).

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshavsky et al., *J. Am. Chem. Soc.*, 112, 9438 (1990); Ushida et al., *J. Phys. Chem.*, 95, 5382 (1992).

Suitable nanoparticles are also commercially available from, e.g., Ted Pella, Inc. (gold), Amersham Corporation (gold) and Nanoprobes, Inc. (gold).

Presently preferred for use in detecting nucleic acids are gold nanoparticles such as the ones described in International Application Number PCT/US01/01190, filed Jan. 12, 2001, and U.S. Pat. No. 6,506,564, issued Jan. 14, 2003, which are both incorporated hererin by reference in their entirety. Gold colloidal particles have high extinction coefficients for the bands that give rise to their beautiful colors. These intense colors change with particle size, concentration, interparticle distance, and extent of aggregation and shape (geometry) of the aggregates, making these materials particularly attractive for colorimetric assays. For instance, hybridization of oligonucleotides attached to gold nanoparticles with oligonucleotides and nucleic acids results in an immediate color change visible to the naked eye (see, e.g., the Examples).

In order to bind the polyanionic polymer conjugates to the nanoparticles, the polyanionic polymer conjugates are contacted with the nanoparticles in water for a time sufficient to allow at least some of the polyanionic polymer conjugates to bind to the nanoparticles by means of the functional groups. Such times can be determined empirically. For instance, it has been found that a time of about 12-24 hours gives good results. Other suitable conditions for binding of the polyanionic polymer conjugates can also be determined empirically. For instance, a concentration of about 10-20 nM nanoparticles and incubation at room temperature gives good results.

A recognition probe X' may be attached to a polyanion before the polyanion is attached to a nanoparticle. In this embodiment, X in the polyanion conjugate represents either -Q-X' or X'. Alternatively, a recognition group X' may be attached to a polyanion after the polyanion has already been attached to a nanoparticle.

A preferred method for attaching polyanionic polymer conjugates to a nanoparticle is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures of which are incorporated by reference in their entirety.

The aging process provides nanoparticle probes with enhanced stability and selectivity. The polyanionic polymer conjugates are contacted with the nanoparticles in water for a time sufficient to allow at least some of the polyanionic polymer conjugates to bind to the nanoparticles by means of the functional groups. Such times can be determined empirically. For instance, it has been found that a time of about 12-24 hours gives good results. Other suitable conditions for binding of the polyanionic polymer conjugates can also be determined empirically. For instance, a concentration of about 10-20 nM nanoparticles and incubation at room temperature gives good results.

Next, at least one salt is added to the water to form a salt solution. The salt can be any suitable water-soluble salt. For instance, the salt may be sodium chloride, lithium chloride, potassium chloride, cesium chloride, ammonium chloride, sodium nitrate, lithium nitrate, cesium nitrate, sodium acetate, lithium acetate, cesium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the polyanionic polymer conjugates from each other and, either the electrostatic attraction of the negatively-charged polyanionic polymer conjugates for positively-charged nanoparticles, or the electrostatic repulsion of the negatively-charged polyanionic polymer conjugates from negatively-charged nanoparticles. Gradually reducing the electrostatic attraction and repulsion by adding the salt gradually over time provides the highest surface density of polyanionic polymer conjugates on the nanoparticles. Suitable ionic strengths can be determined empirically for each salt or combination of salts. A final concentration of sodium chloride of from about 0.1 M to about 3.0 M in phosphate buffer, preferably with the concentration of sodium chloride being increased gradually over time, has been found to give good results.

After adding the salt, the polyanionic polymer conjugates and nanoparticles are incubated in the salt solution for an additional period of time sufficient to allow sufficient additional polyanionic polymer conjugates to bind to the nanoparticles to produce the stable nanoparticle- polyanion polymer probes. The time of this incubation can be determined empirically. A total incubation time of about 24-48, preferably 40 hours, gives good results (this is the total time of incubation; as noted above; the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results. The solution is then centrifuged and the nanoparticle probes processed as desired.

The probes produced by use of the "aging" step are more stable than those produced without the "aging" step. As noted above, this increased stability is due to the increased density of the polyanionic polymer conjugates on the surfaces of the nanoparticles which is achieved by the "aging" step. The surface density achieved by the "aging" step will depend on the size and type of nanoparticles and on the length, and concentration of the polyanionic polymer conjugates. A surface density adequate to make the nanoparticles stable and the conditions necessary to obtain it for a desired combination of nanoparticles and polyanionic polymer conjugates can be determined empirically.

Nanoparticles having polyanionic polymer conjugates of the invention attached thereto (referred to herein as "nanoparticle probes" or "nanoparticle conjugates") have a variety of uses. For instance, they can be used as probes to detect or quantitate analytes. See, e. g., PCT application WO 98/04740; PCT application WO 98/21587; Storhoff et al., J. Clust. Sci., 8: 179 (1997); Brousseau et al., J. Am. Chem. Soc., 120: 7645 (1998); Freeman et al., Science, 267: 1629 (1995); Zhu et al., J. Am. Chem. Soc., 119: 235 (1997); Mirkin et al., Nature, 382: 607 (1996); Elghanian et al., Science, 277: 1078 (1997); Storhoff et al., J. Am. Chem. Soc., 120: 1959 (1998). Analytes that can be detected or quantitated according to the invention include polysaccharides, lipids, lipopolysaccharides, proteins, glycoproteins, lipoproteins, nucleoproteins, peptides, oligonucleotides, and nucleic acids. Specific analytes include antibodies, immunoglobulins, albumin, hemoglobin, coagulation factors, peptide and protein hormones (e.g., insulin, gonadotropin, somatotropin), non-peptide hormones, interleukins, interferons, other cytokines, peptides comprising a tumor-specific epitope (i.e., an epitope found only on a tumor-specific protein), cells (e. g., red blood cells), cell surface molecules (e. g., CD antigens, integrins, cell receptors), microorganisms (viruses, bacteria, parasites, molds, and fungi), fragments, portions, components or products of microorganisms, small organic molecules (e. g., digoxin, heroin, cocaine, morphine, mescaline, lysergic acid, tetrahydrocannabinol, cannabinol, steroids, pentamidine, and biotin), etc. Nucleic acids and oligonucleotides that can be detected or quantitated include genes (e. g., a gene associated with a particular disease), viral RNA and DNA, bacterial DNA, fungal DNA, mammalian DNA (e. g., human DNA), cDNA, mRNA, RNA and DNA fragments, oligonucleotides, synthetic oligonucleotides, modified oligonucleotides, single-stranded and double-stranded nucleic acids, natural and synthetic nucleic acids, etc.

To serve as probes, the nanoparticle probes of the invention include the recognition probe section X', as part of the polyanionic polymer conjugates attached thereto, which allows the nanoparticle probes to bind specifically to the analyte. Suitable recognition probes X' and methods of making them are well known in the art. For instance, essentially any analyte can be detected or quantitated using antibodies specific for the analyte. In addition, any molecule which binds specifically to the analyte can be used, and many such molecules are known in the art. For instance, nucleic acids can be detected or quantitated using oligonucleotides having a sequence which is complementary to at least a portion of the analyte nucleic acid. Also, lectins can be used to detect or quantitate polysaccharides and glycosylated proteins. As another example, a receptor can be used to detect its ligand and vice versa. Many other suitable recognition probes X' are known.

To perform an assay according to the invention, a sample suspected of containing an analyte is contacted with nanoparticle probes having recognition probes X' attached thereto. Any type of sample can be used. For instance, the sample may be a biological fluid (e.g., serum, plasma, blood, saliva, and urine), cells, cell lysates, tissues, libraries of compounds (e.g., organic chemicals or peptides), solutions containing PCR components, etc. Conditions and formats for performing such assays are well known in the art (see, e.g., the references cited above) or can be determined empirically by those of ordinary skill in the art. Finally, the property or properties of the nanoparticles is (are) detected or measured in order to detect or quantitate the analyte. Preferably, the property is redox activity or optical activity (e.g., fluorescence or color as described below). Methods of detecting and measuring these properties are well known in the art.

One example of a method for detecting a target analyte wherein the target analyte is a nucleic acid comprises contacting the nucleic acid with one or more types of nanoparticle probes of the invention. The nucleic acid to be detected has at least two portions. The lengths of these portions and the distance(s), if any, between them are chosen so that when the recognition probes on the nanoparticle probes hybridize to the nucleic acid, a detectable change occurs. These lengths and distances can be determined empirically and will depend on the type of particle used and its size and the type of electrolyte which will be present in solutions used in the assay (as is known in the art, certain electrolytes affect the conformation of nucleic acids).

Also, when a nucleic acid is to be detected in the presence of other nucleic acids, the portions of the nucleic acid to which the recognition probes on the nanoparticle probes are to bind must be chosen so that they contain sufficient unique sequence so that detection of the nucleic acid will be specific. Guidelines for doing so are well known in the art.

Although nucleic acids may contain repeating sequences close enough to each other so that only one type of nanoparticle probe need be used, this will be a rare occurrence. In general, the chosen portions of the nucleic acid will have different sequences and will be contacted with nanoparticles having polyanionic polymer conjugates attached thereto, wherein the conjugates carry two or more different recognition probes, preferably attached to different nanoparticles. Additional portions of the DNA could be targeted with corresponding nanoparticles. Targeting several portions of a nucleic acid increases the magnitude of the detectable change.

The contacting of the nanoparticle probes with the nucleic acid takes place under conditions effective for hybridization of the recognition probes on the polyanionic polymer conjugates attached to the nanoparticles with the target sequence(s) of the nucleic acid. These hybridization conditions are well known in the art and can readily be optimized for the particular system employed. See, e.g., Sambrook et al., *Molecular Cloning: A Laboratory Manual* (2nd ed. 1989). Preferably stringent hybridization conditions are employed.

Faster hybridization can be obtained by freezing and thawing a solution containing the nucleic acid to be detected and the nanoparticle probes. The solution may be frozen in any convenient manner, such as placing it in a dry ice-alcohol bath for a sufficient time for the solution to freeze (generally about 1 minute for 100 microliters of solution). The solution must be thawed at a temperature below the thermal denaturation temperature, which can conveniently be room temperature for most combinations of nanoparticle probes and nucleic acids. The hybridization is complete, and the detectable change may be observed, after thawing the solution.

The rate of hybridization can also be increased by warming the solution containing the nucleic acid to be detected and the nanoparticle probes to a temperature below the dissociation temperature (Tm) for the complex formed between the recognition probes on the nanoparticle probes and the target nucleic acid. Alternatively, rapid hybridization can be achieved by heating above the dissociation temperature (Tm) and allowing the solution to cool.

The rate of hybridization can also be increased by increasing the salt concentration (e.g., from 0.1 M to 1 M NaCl). The rate of the reaction can also be increased by adding a volume exclusion reagent such as dextran sulfate.

The detectable change that occurs upon hybridization of the recognition probes on the nanoparticle probes to the nucleic acid may be an optical change (e.g. color change), the formation of aggregates of the nanoparticles, or the precipitation of the aggregated nanoparticles. The optical changes can be observed with the naked eye or spectroscopically. The formation of aggregates of the nanoparticles can be observed by electron microscopy or by nephelometry. The precipitation of the aggregated nanoparticles can be observed with the naked eye or microscopically. Preferred are color changes observable with the naked eye.

The observation of a color change with the naked eye can be made more readily against a background of a contrasting color. For instance, when gold nanoparticles are used, the observation of a color change is facilitated by spotting a sample of the hybridization solution on a solid white surface (such as silica or alumina TLC plates, filter paper, cellulose nitrate membranes, and nylon membranes, preferably a nylon membrane) and allowing the spot to dry. Initially, the spot retains the color of the hybridization solution (which ranges from pink/red, in the absence of hybridization, to purplish-red/purple, if there has been hybridization). On drying at room temperature or 80° C. (temperature is not critical), a blue spot develops if the polyanion polymer-nanoparticle conjugates had been linked by hybridization with the target nucleic acid prior to spotting. In the absence of hybridization (e.g., because no target nucleic acid is present), the spot is pink. The blue and the pink spots are stable and do not change on subsequent cooling or heating or over time. They provide a convenient permanent record of the test. No other steps (such as a separation of hybridized and unhybridized nanoparticle probes) are necessary to observe the color change. The color change may be quantitated by recording the plate image with an optical scanning device such as a flatbed scanner or CCD camera, and analyzing the amount and type of color of each individual spot. Alternatively, a color filter (e.g. red filter) may be used to filter out specific colors so that the signal intensity of each spot may be recorded and analyzed.

An alternate method for easily visualizing the assay results is to spot a sample of nanoparticle probes hybridized to a target nucleic acid on a glass fiber filter (e.g., Borosilicate Microfiber Filter, 0.7 micron pore size, grade FG75, for use with gold nanoparticles 13 nm in size), while drawing the liquid through the filter. Subsequent rinsing with water washes the excess, non-hybridized nanoparticle probes through the filter, leaving behind an observable spot comprising the aggregates generated by hybridization of the recognition probes on the nanoparticle probes with the target nucleic acid (retained because these aggregates are larger than the pores of the filter). This technique may provide for greater sensitivity, since an excess of nanoparticle probes can be used.

Binding may also be detected by light scattering techniques such as those described in U.S. provisional application No. 60/474,569, filed May 30, 2003, which is incorporated herein by reference in its entirety. In such methods, binding analytes, e.g., nucleic acids or proteins, can be detected through light scattering techniques, where a change in light scattering caused by the formation of nanoparticle label complexes within the penetration depth of an evanescent wave of a wave guide signals the presence of analyte.

Some embodiments of the method of detecting nucleic acid utilize a substrate. By employing a substrate, the detectable change (the signal) can be amplified and the sensitivity of the assay increased.

Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates).

In one embodiment of the method of detecting nucleic acid using a substrate, oligonucleotides are attached to the substrate. The oligonucleotides can be attached to the substrates as described in, e.g., Chrisey et al., Nucleic Acids Res., 24, 3031-3039 (1996); Chrisey et al., Nucleic Acids Res., 24, 3040-3047 (1996); Mucic et al., Chem. Commun., 555 (1996); Zirnnermann and Cox, Nucleic Acids Res., 22, 492 (1994); Bottomley et al., J. Vac. Sci. Technol. A, 10, 591 (1992); and Hegner et al., FEBS Lett., 336, 452 (1993).

The oligonucleotides attached to the substrate have a sequence complementary to a first portion of the sequence of a nucleic acid to be detected. The nucleic acid is contacted with the substrate under conditions effective to allow hybridization of the oligonucleotides on the substrate with the nucleic acid. In this manner the nucleic acid becomes bound to the substrate. Any unbound nucleic acid is preferably washed from the substrate before adding nanoparticle probes.

Next, the nucleic acid bound to the substrate is contacted with a first type of nanoparticle probes. The recognition probes on the nanoparticle probes have a sequence complementary to a second portion of the sequence of the nucleic acid, and the contacting takes place under conditions effective to allow hybridization of the recognition probes on the nanoparticles with the nucleic acid. In this manner the first type of nanoparticle probes become bound to the substrate. After the nanoparticle probes are bound to the substrate, the substrate is washed to remove any unbound nanoparticle probes and nucleic acid.

The recognition probes on the first type of nanoparticle probes may all have the same sequence or may have different sequences that hybridize with different portions of the nucleic acid to be detected. When recognition probes having different sequences are used, each nanoparticle may have all of the different recognition probes attached to it or, preferably, the different recognition probes are attached to different nanoparticles. Alternatively, the recognition probes on each of the first type of nanoparticle probes may have a plurality of different sequences, at least one of which must hybridize with a portion of the nucleic acid to be detected.

The first type of nanoparticle probes bound to the substrate are optionally contacted with a second type of nanoparticle probes. These recognition probes (on the second type of nanoparticle probes) have a sequence complementary to at least a portion of the sequence(s) of the recognition probes on the first type nanoparticle probes, and the contacting takes place under conditions effective to allow hybridization of the recognition probes on the first type of nanoparticle probes with those on the second type of nanoparticle probes. After the nanoparticles are bound, the substrate is preferably washed to remove any unbound conjugates.

The combination of hybridizations produces a detectable change. The detectable changes are the same as those described above, except that the use of the second type of nanoparticle probes provides multiple hybridizations which result in an amplification of the detectable change. In particular, since each of the first type of nanoparticle probes has multiple recognition probes (having the same or different sequences) attached to it, each of the first type of nanoparticle probes can hybridize to a plurality of the second type of nanoparticle probes. Also, the first type of nanoparticle probes may be hybridized to more than one portion of the nucleic acid to be detected. The amplification provided by the multiple hybridizations may make the change detectable for the first time or may increase the magnitude of the detectable change. This amplification increases the sensitivity of the assay, allowing for detection of small amounts of nucleic acid.

If desired, additional layers of nanoparticles can be built up by successive additions of the first and second types of nanoparticle probes. In this way, the number of nanoparticles immobilized per molecule of target nucleic acid can be further increased with a corresponding increase in intensity of the signal.

In one embodiment for detection of non-nucleic acid analytes (see for example U.S. patent application Ser. No. 09/820,279, filed Mar. 28, 2001, and International application PCT/01/10071, filed Mar. 28, 2001, each of which is incorporated herein by reference) the analyte may be bound directly or indirectly, via covalent or non-covalent interactions, to a substrate. The substrates are the same type as described above. For indirect binding, the analyte can be bound to the substrate via a linker, e.g., an oligonucleotide or other spacer molecule. Alternatively, the analyte may be modified by binding it to an oligonucleotide having a sequence that is complementary to at least a portion of the sequence of a capture probe, such as an oligonucleotide, bound to a substrate. The nanoparticle probes having recognition probes that can hybridize to the analyte are then contacted with the substrate under conditions effective to allow the specific binding of the recognition probes to the analyte bound to the substrate and the presence of the analyte can be visually detected either by formation of a spot on the substrate or through the use of staining material such as silver on gold stain.

In another method for detecting analytes, the target analyte can be modified by attaching the analyte to a polyanionic polymer conjugate as the recognition probe and attaching the polyanionic polymer conjugate to a nanoparticle. Thereafter, the modified nanoparticle probe is contacted with a substrate having a second member of the recognition couple bound thereto. The presence of the analyte can be visually detected either by formation of a spot on the substrate or through the use of staining material such as silver on gold stain.

In yet another method for detecting analytes, the target analyte is modified by binding it to an oligonucleotide having a sequence that is complementary to at least a portion of a sequence of a recognition probe on a nanoparticle probe. The modified target is then coupled to the recognition probe on the nanoparticle by contacting the modified target and the nanoparticle under conditions effective for hybridization between the oligonucleotide bound to the target and the recognition probe on the nanoparticle. The hybridized complex is then contacted with a substrate having a recognition group for the analyte bound thereto. The presence of the analyte can be visually detected either by formation of a spot on the substrate or through the use of staining material such as silver on gold stain.

When a substrate is employed, a detectable change can be produced or enhanced by staining. Staining material, e.g., gold, silver, etc., can be used to produce or enhance a detectable change in any assay performed on a substrate, including those described above. For instance, silver staining can be employed with any type of nanoparticles that catalyze the reduction of silver. Preferred are nanoparticles made of noble metals (e.g., gold and silver). See Bassell, et al., *J. Cell Biol.*, 126, 863-876 (1994); Braun-Howland et al., *Biotechniques*, 13, 928-931 (1992). If the nanoparticles being employed for the detection of analyte do not catalyze the reduction of silver, then silver ions can be complexed to the target analyte to catalyze the reduction. See Braun et al., *Nature*, 391, 775 (1998). Also, silver stains are known which can react with the phosphate groups on nucleic acids.

The invention further provides kits for detecting the presence or absence of a target analyte in a sample comprising. A kit may comprise a container holding polyanionic polymer conjugates having recognition probes attached thereto. A kit may also comprise a container holding polyanionic polymer conjugates having recognition probes, wherein the polyanionic polymer conjugates are attached to nanoparticles. The kits may also contain other reagents and items useful for performing the assays. The reagents may include controls, standards, PCR reagents, hybridization reagents, buffers, etc. Other items which be provided as part of the kit include reaction devices (e. g., test tubes, microtiter plates, solid surfaces (possibly having a capture molecule attached thereto), syringes, pipettes, cuvettes, containers, etc.

The following examples are illustrative of the invention but do not serve to limit its scope.

EXAMPLES

To illustrate the invention a representative non-nucleotide based polyanionic polymer conjugate was prepared, Scheme 1. The conjugate contains three parts: 1) a linker such as a steroid cyclic disulfide anchor that is used as a linker for the gold nanoparticle surface,[7] 2) a phosphate based polyanion backbone with a bridging group (e.g. polyethylene glycol) designed to provide nanoparticle stabilization, and 3) a fluorescein label as a tag for purification and quantitation.

Scheme 1

Polyanion 1 a. Preparation and Purification of a Polyanion Polymer

Figure 1:
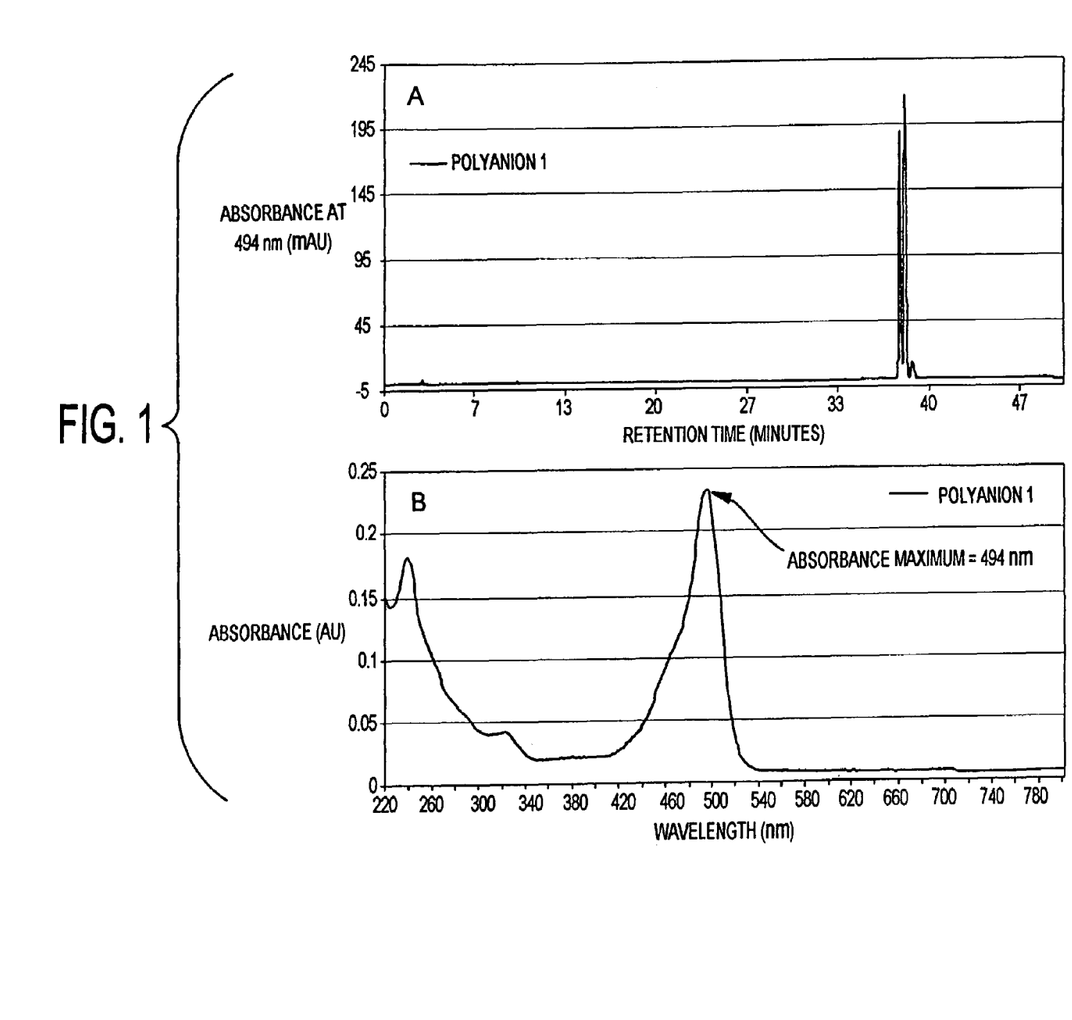
FIG. 1A is an HPLC chromatogram of polyanion 1 after purification.
FIG. 1B is a UV-visible spectrum of polyanion 1 after purification.

The molecule was prepared using standard phosphoramidite chemistry on an Expedite 8909 synthesizer and purified by reverse phase HPLC using standard conditions[5] while monitoring the 494 nm absorption maximum of the fluorescein tag. The purified product exhibited a doublet at retention times of 37.8 and 38.2 minutes respectively when monitored at 494 nm indicating the presence of both the steroid cyclic disulfide anchor and the fluorescein tag, FIG. 1. The retention time and the doublet observed for the product are consistent with oligonucleotides modified with the steroid cyclic disulfide linker, and the absorbance at 494 nm is characteristic for the fluorescein chromophore. The purified polyanion product was quantitated using the absorbance at 494 nm ($\epsilon_{494}$=75000 M$^{-1}$ cm$^{-1}$).

b. Loading Onto Nanoparticles

Figure 2:
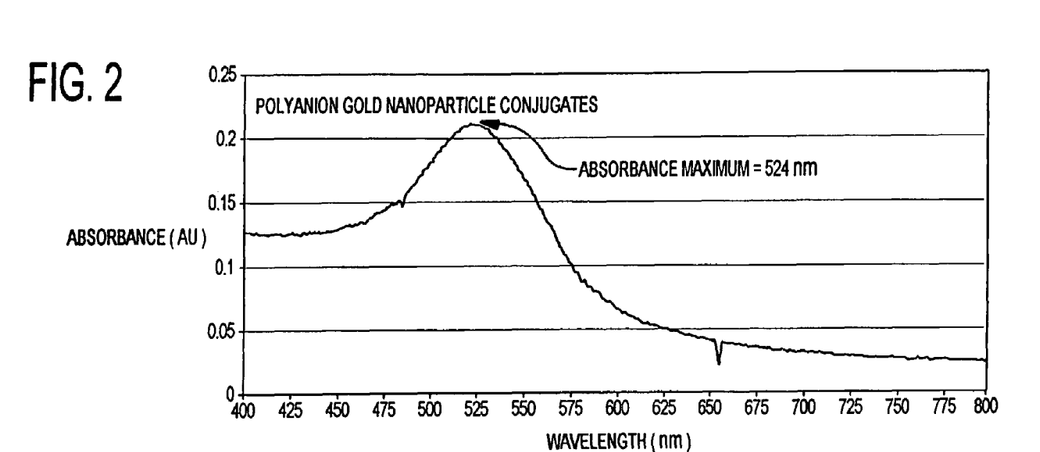
FIG. 2 is a visible absorbance spectrum of gold nanoparticle-polyanion 1 conjugates after loading and isolation.

The polyanion was loaded onto ~16.5 nm diameter gold nanoparticles prepared via the citrate method[6] using the following procedure. The gold nanoparticle solution (2 mL, ~14 nM) was mixed with polyanion DNA (final concentration=3.6 uM) and buffered to pH 7 at 10 mM phosphate (pH 7) and incubated at room temperature overnight. The salt concentration was subsequently adjusted to 0.1 M phosphate buffered saline (PBS; 10 mM phosphate, 0.1 M NaCl, pH 7) using 4 M PBS (10 mM phosphate, 4 M NaCl, pH 7), and the solution was incubated for >40 hours. The probes were isolated via centrifugation (13000 rpm×25 minutes), washed once with water, and redispersed to a final gold nanoparticle concentration of 10 nM using 10 mM phosphate (pH 7) buffer, 0.01% azide. The polyanion coated gold nanoparticles were stable to centrifugation and 0.1 M PBS as evidenced by the UV-vis spectrum after isolation which exhibits an absorption maximum of 524 nm which is characteristic of DNA-modified gold nanoparticles prepared by the same procedure, FIG. 2.[5]

c. Quantitation of Polyanion Conjugates Attached to the Gold Nanoparticles

Figure 3:
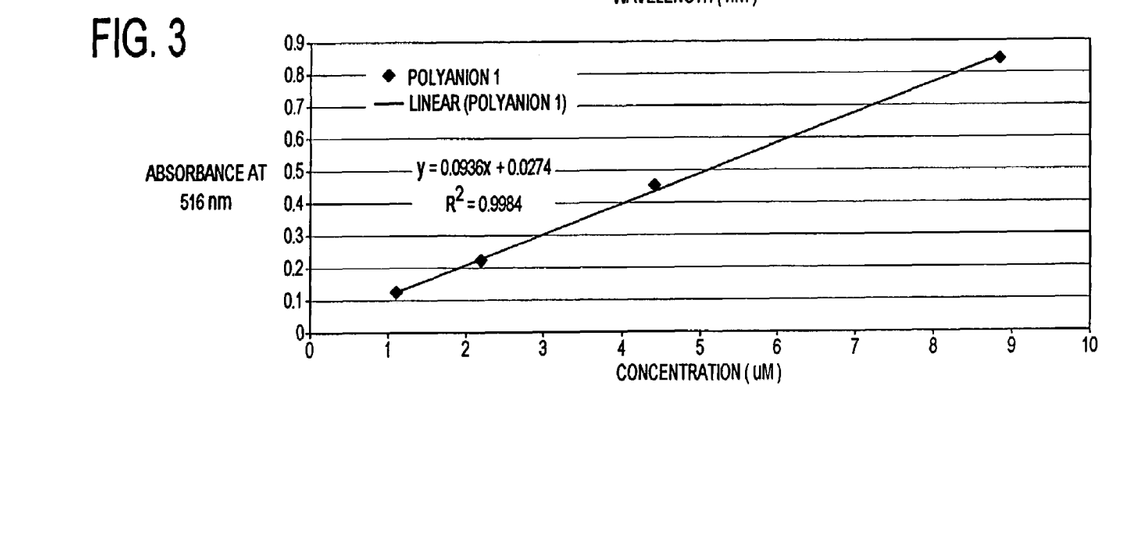
FIG. 3 is a graph depicting a standard curve used to measure the number of polyanion molecules per gold particle.

The polyanion conjugates attached to the gold nanoparticles were quantitated using the absorbance signature associated with the fluorescein to demonstrate that the polyanion conjugates were attached to the nanoparticles. To quantitate the fluorescein signature, the gold particles were dissolved to remove the absorbance associated with the particles using the following procedure. The polyanion conjugated gold nanoparticles (200 ul, 10 nM) were mixed with 0.1 M $I_2$ (10 ul) and incubated at room temperature for 10 minutes which dissolved the gold nanoparticles turning the solution a yellowish color. A solution of 0.1 M sodium thiosulfate (20 uL) was added to reduce the iodine and incubated for five minutes at room temperature. The absorbance of this solution was measured at 516 run (absorption maxima of fluorescein as modified by treatment with $I_2$/thiosulfate) without dilution to quantitate the amount of flourescein present and compared to a standard concentration curve of the polyanion (without gold nanoparticle) prepared using the same procedure, FIG. 3. The standard curve for the concentration range of interest was linear. Using the equation from the best fit line, the polyanion concentration from the gold probe solution was measured to be 1.51 uM (Absorbance at 516 nm=0.17 AU). From the starting ~10 nM probe solution, this equates to ~151 polyanion molecules per particle.

d. Stability of Polyanion Conjugates Attached to the Gold Nanoparticles

Figure 4:
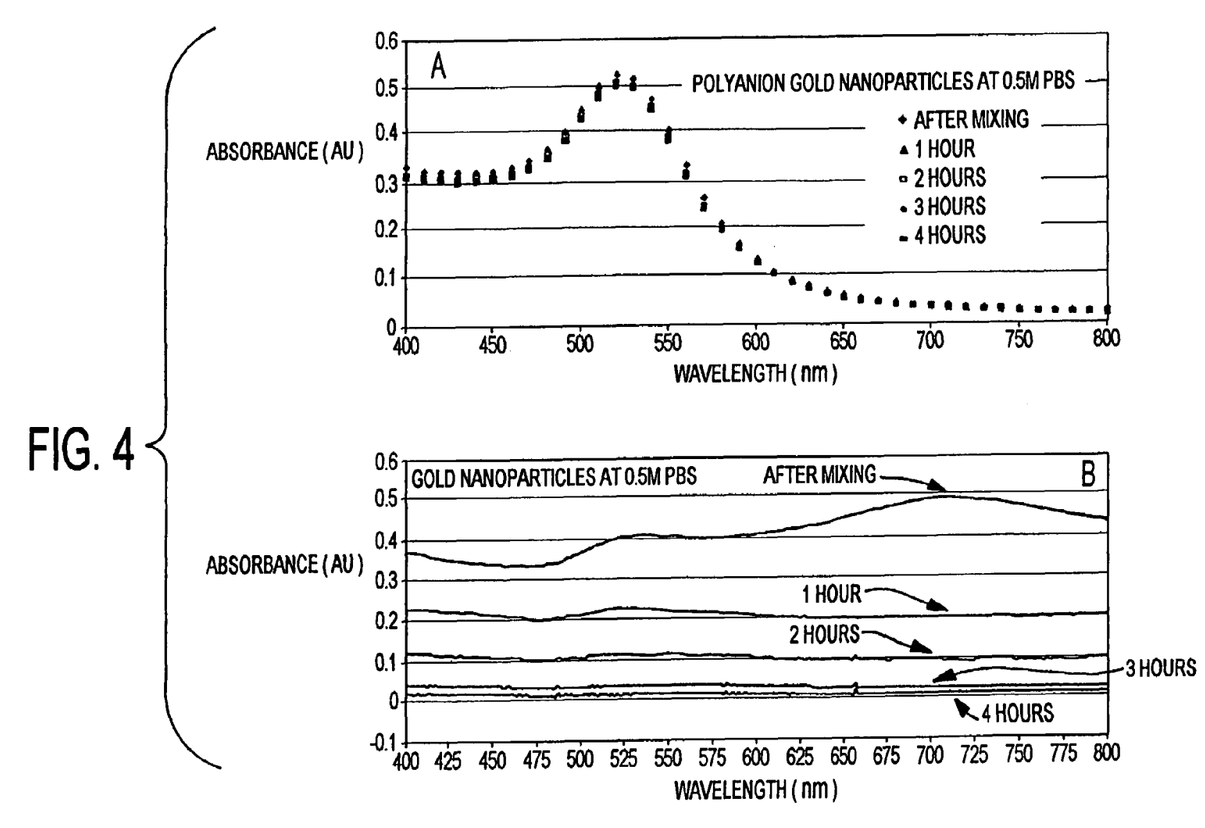
FIG. 4A is a graph indicating stability of polyanion 1-gold nanoparticle conjugates at 0.5 M PBS.
FIG. 4B is a graph of stability of citrate modified nanoparticles at 0.5 M PBS.

Stability towards elevated electrolyte concentrations as well as temperature is critical for biomolecule assays which are typically performed under such conditions. The robustness of the polyanion gold conjugates as compared to the citrate stabilized gold nanoparticles was tested by first monitoring the stability of the two solutions at 0.5 M PBS over a four hour time period, FIG. 4. In this assay, the polyanion probe solution (5 nM, 100 uL) was mixed with 100 ul of 1 M PBS (0.5 M PBS final concentration) at room temperature, and the UV-vis spectrum was monitored as a function of time. This process was repeated for the citrate modified gold nanoparticles adjusted to 5 nM particle concentration in 10 mM phosphate pH 7. The polyanion gold conjugates exhibit little loss in signal over the four hour time period and no detectable shifts in the UV-visible spectrum. By contrast, the citrate modified gold nanoparticles exhibit a red shift within 15 seconds of mixing indicating instability followed by almost total loss of signal over the four hour time period. This data clearly demonstrates that the polyanion conjugated gold nanoparticles exhibit significantly enhanced stability when compared to the citrate modified gold nanoparticles. These studies therefore provide data that indicate that the polyanion stabilized gold nanoparticles may be used under conditions typically employed for detection of biomolecules such as DNA and at gold nanoparticle concentrations that may be detected optically or via other methods.[5] This enhanced stability clearly distinguishes the polyanion gold probes described here from previously prepared polyanion gold probe conjugates.[1,2]

Figure 5:
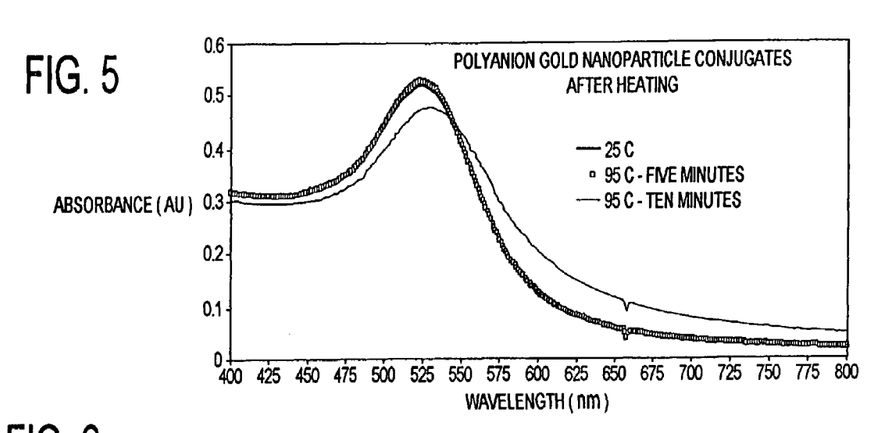
FIG. 5 is a graph indicating stability of polyanion 1-gold nanoparticle conjugates at 0.5 M PBS after heating.

The thermal stability of the polyanion gold nanoparticle conjugates (prepared in 0.5 M PBS as described in FIG. 4 assay) was tested by heating the solution to 95° C. for five minutes and 10 minutes and comparing the resulting UV-visible spectrum to the same solution that had not undergone heat treatment, FIG. 5. Under these conditions, the polyanion gold nanoparticle conjugates are stable for five minutes at 95° C. as little change in the UV-visible spectrum was observed. After heating for 10 minutes, a slight red shift in the UV-visible spectrum was observed indicating slight instability to prolonged heating. Nonetheless, these data demonstrate that the polyanion gold nanoparticle conjugates are stable to extreme temperatures for short periods of time (<five minutes).

e. Detection of Biomolecules

After demonstrating that polyanions were good stabilizers for gold nanoparticles, the next goal was to demonstrate utility of the polyanion probes in the detection of biomolecules. The biotin/Streptavidin binding pair was chosen as a model system to demonstrate this principle due to the high affinity of the binding and the multiple binding sites associated with Streptavidin. Polyanion sequence 6 was synthesized using standard phosphoramidite chemistry with a Biotin-TEG CPG support for biotin incorporation, Scheme 2. This Polyanion can be segmented into four distinct portions 1) the steroid disulfide anchor[7], 2) a Nitroindole UV tag used for purification and quantification, 3) a phosphate-based polyanion backbone (e.g., a polyethylene glycol based spacer), and 4) the tetraethylene glycol Biotin complex used for Streptavidin recognition.

Polyanion 6 was conjugated to ~30 nm diameter gold particles purchased from BBI, Inc (BBI measured mean diameter=30.9 nm by TEM). The initial solution of gold colloid (0.33 nM) was mixed with Polyanion 6 (final concentration=800 nM) and incubated for 64 hrs at room temperature. The probes were isolated from solution by centrifugation (5,000 rpm for 20 minutes), washed once in water and redispersed to 1.7 nM gold particle concentration in 10 mM Phosphate (pH 7) buffer, 0.01% Azide.

Figure 7:
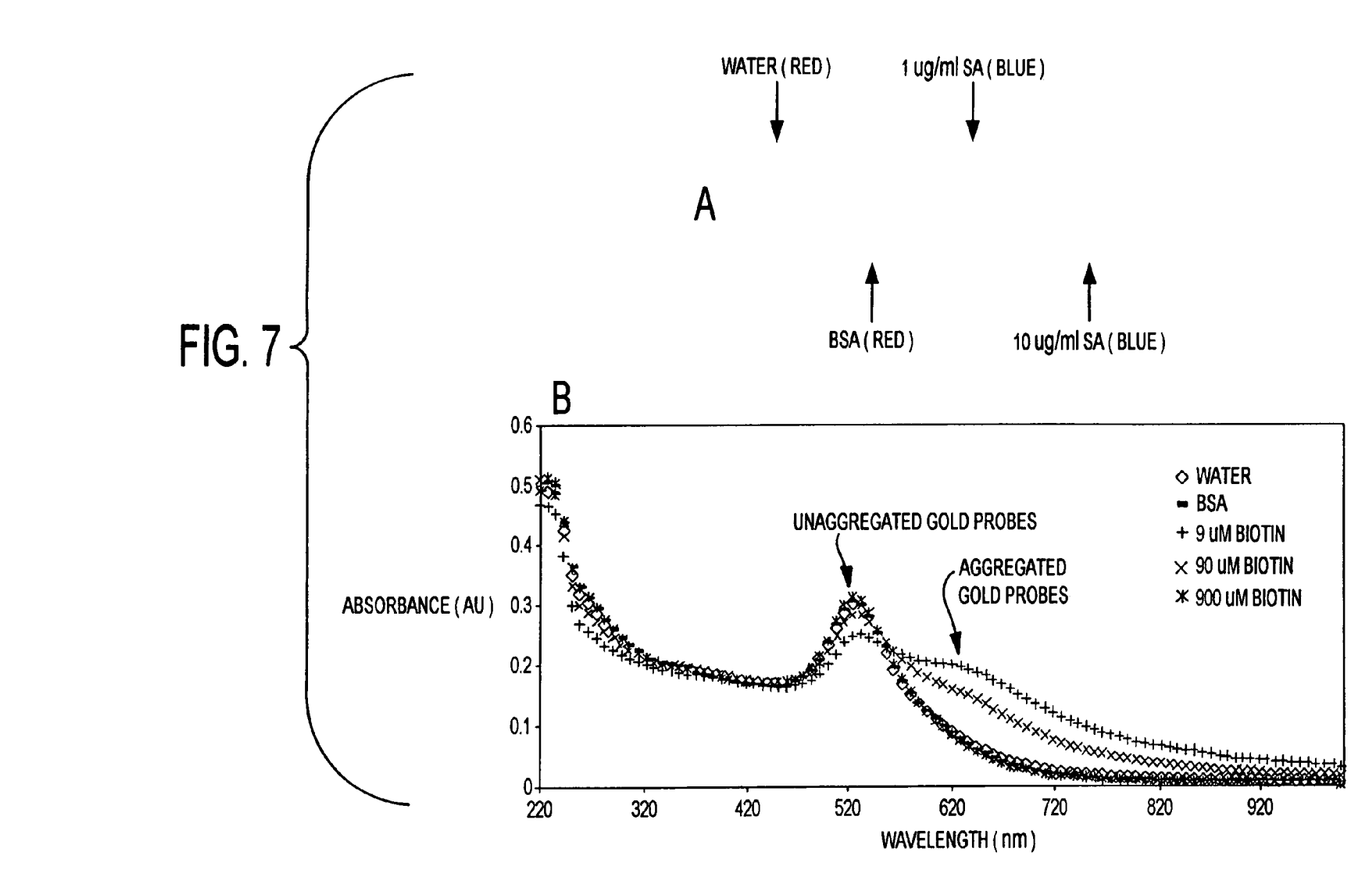
FIG. 7A shows a reversed phase plate which exhibits spot test results from solutions of polyanion 6 incubated with Streptavidin or control solutions.
FIG. 7B is a UV-vis spectrum of polyanion 6 incubated with Streptavidin or control solutions.

In previous experiments, it has been demonstrated that DNA-modified gold nanoparticle probes may be used to detect biomolecules such as DNA in solution by monitoring color changes associated with particle aggregation either in solution or by depositing aliquots of the solution onto a reverse phase plate and drying, which is referred to as the spot test.[5] To demonstrate that polyanion gold nanoparticle conjugates may be used for biomolecule detection, a streptavidin binding experiment was performed using the polyanion 6 conjugated gold nanoparticle probes which contain biotin functionalities. In a typical experiment, the probes (24 μl, 1.1 nM) were combined with one of the following reagents (3 μl): water, Bovine Serum Albumin (4 μg/ml), or Streptavidin (1 μg /ml, 10 μg/ml), and diluted to 0.055 M NaCl using 20 ul of 1x PBS (0.15 M Sodium Chloride) and 7 ul of water. After a fifteen minute incubation at room temperature, a 3 ul aliquot of the solution was spotted onto a reverse phase plate and dried to monitor color changes associated with particle aggregation, FIG. 7.A.[5] Both solutions containing the Streptavidin exhibited a colorimetric transition from red to purple or blue which indicates Streptavidin induced particle aggregation. The control solutions containing the protein BSA or no target exhibited a red color when spotted indicating that no significant aggregation had taken place. The colorimetric changes associated with the Streptavidin induced polyanion probe aggregation could also be monitored by UV-visible spectroscopy, FIG. 7.B The UV-vis data clearly shows the characteristic red shift associated with particle aggregation in the presence of Streptavidin, but not in the presence of the control protein BSA.

To further demonstrate the specificity of the biotinylated gold probe/Streptavidin reaction, a competitive binding experiment was performed where the Streptavidin was pre- Scheme 2

Polyanion 6

Figure 6:
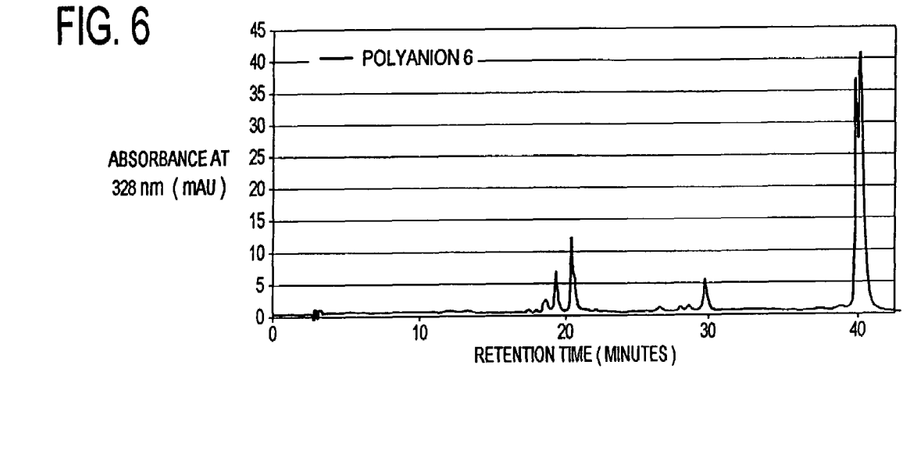
FIG. 6 is an HPLC chromatogram of polyanion 6 after purification.
Figure 8:
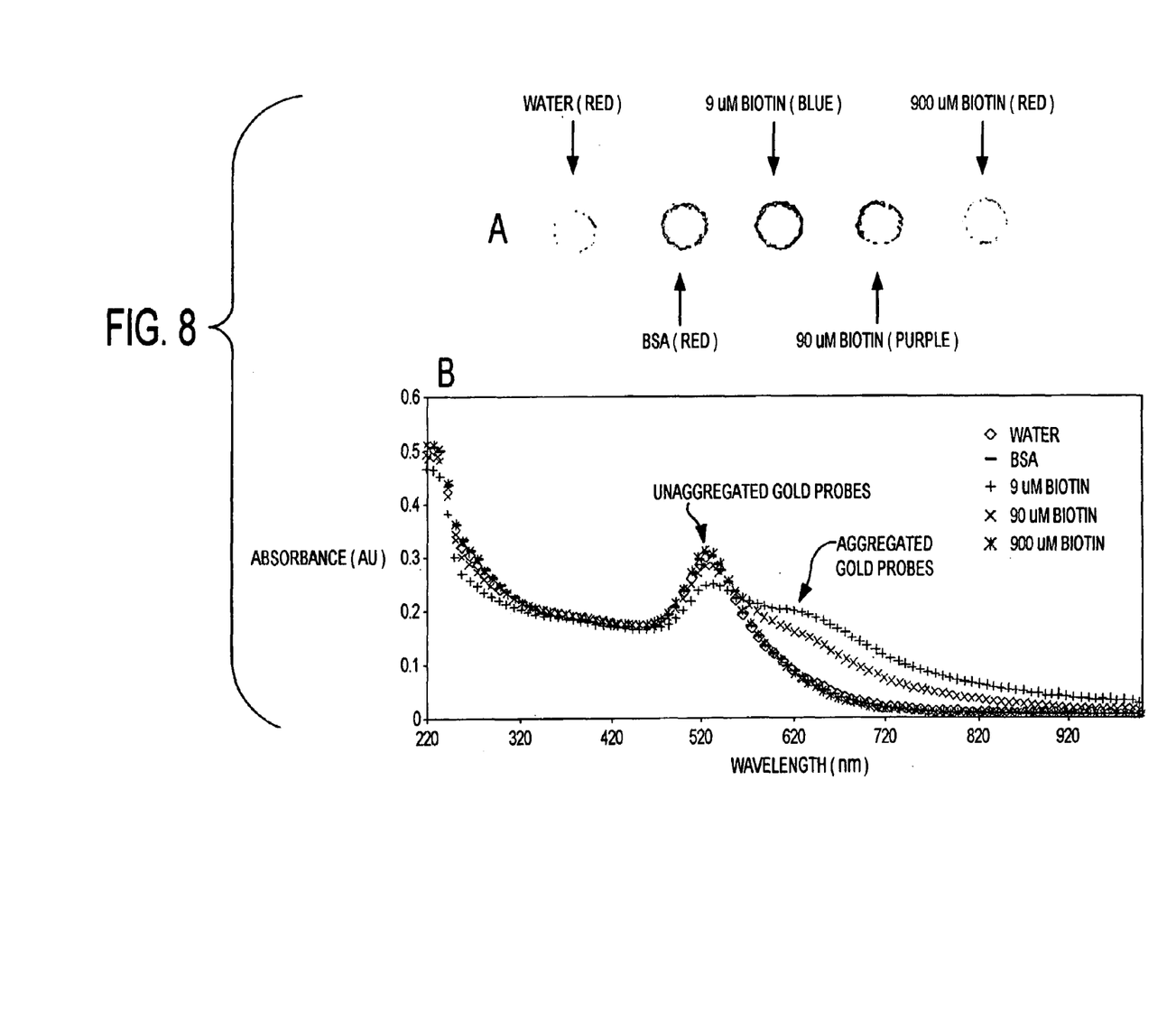
FIG. 8A shows spot test results for free d-biotin/polyanion 6 competitive binding experiment for Streptavidin.
FIG. 8B is a UV-visible spectrum of free d-biotin/polyanion 6 competitive binding experiment for Streptavidin.

Reverse phase HPLC was used to purify polyanion 6 using the same protocol as for Polyanion 1 while monitoring the absorption at 265 nm and 328 nm, characteristic absorbance maxima of the nitroindole tag. Polyanion 6 exhibited a doublet with retention times of 39.8 and 40.1 minutes at both monitored wavelengths indicating the presence of the steroid disulfide linker and the nitroindole tag, FIG. 6.

incubated with free d-Biotin prior to probe incubation. In a typical experiment, Streptavidin solutions (3 ul of 1 μg/ml) were prepared with a dilution series of free d-Biotin (4.6 μl of 900 μM, 90 μM and 9 μM) and diluted with water (10 μl total volume). These solutions were incubated at room temperature for 10 minutes then added to a solution of Polyanion 6 (24 μl of 1.1 nM gold probes) and buffered with 1X PBS (20 μl of 0.15 M Sodium Chloride). After a fifteen minute incubation, a 3 ul aliquot of the sample was placed on a reverse phase TLC plate and allowed to dry, FIG. 8.A. The remainder of the solution was diluted in phosphate buffer (0.1 M Sodium Phosphate pH 7 to 200 μl total volume), and a UV-vis spectrum was recorded, FIG. 8.B. Both the spotted samples and the UV-Vis spectra exhibit a trend of decreasing colorimetric red shifts as the free d-Biotin concentration is increased, with the solution containing the highest concentration of free d-Biotin exhibiting a similar color and UV-vis spectrum when compared to the BSA and no target controls. This trend indicates an increasing inhibition of binding of the biotinylated probes to Streptavidin as the free d-Biotin concentration is increased which results in inhibition of particle aggregation. In conclusion, these experiments clearly demonstrate that functionalized polyanion probes may be used in biomolecule detection schemes based on monitoring a signature associated with the nanoparticle probes.

EXPERIMENTAL. PREPARATION AND CHARACTERIZATION OF POLYANION CONJUGATES

Reagents and General Methods

Spacer phosphoramidite 9, 3'-(6-FAM) CPG, 5-Nitroindole CE phosphoramidite, and Biotin TEG CPG were purchased from Glen Research, Inc (Sterling, Va.). The "steroid-disulfide" phosphoramidite was prepared according to methods developed by Letsinger and coworkers.[7] 16.5 nm diameter gold nanoparticles were prepared via the citrate method.[6] 30.9 nm diameter gold nanoparticles were purchased from BBInternational (Cardiff, UK).

Polyanion synthesis was performed using an Applied Biosystems 8909 nucleic acid synthesizer. High performance liquid chromatography (HPLC) of the polyanions was performed using an Agilent series 1100 HPLC. Electronic absorption spectra were recorded using an Agilent 8453 diode array spectrophotometer. Nanoparticle solutions were centrifuged using a Beckman Coulter Microfuge 18 centrifuge.

Protocols

The polyanion molecules were prepared using standard phospharamidte chemistry.[7] Polyanion 1 was synthesized on a 1 umol scale using a 3'-(6-FAM) CPG support. Polyanion 6 was synthesized on a 1 umol scale using a Biotin TEG CPG support. After synthesis, the CPG-bound polyanions were cleaved from the solid support in 1 mL of concentrated ammonium hydroxide at 55° C. for 14 hours. The ammonia was subsequently blown off using a stream of nitrogen. An HPLC equipped with a reverse-phase Vydac preparative column (5 um, 250×10 mm) was used for polyanion purification. Purification was performed using 0.03 M triethylammonium acetate (TEAA), pH 7 buffer with a 1%/min. gradient of 95% $CH_3CN$/5% 0.03 M TEAA at a flow rate of 4 mL/min. After purification the buffer was evaporated, and the polyanions were resuspended in 25 mM phosphate buffer (pH 7). An analytical HPLC was performed after purification to assess the resulting purity of the polyanions using the same buffer system with a reverse phase Vydac analytical column (5 um, 250×4 mm) at a flow rate of 1 mL/min. The polyanion-gold nanoparticle conjugates were prepared as described in the report section.

REFERENCES (1) M. A. Hayat, Ed., *Colloidal Gold: Principles, Methods, and Applications*, vol. 1 (Academic Press, San Diego, 1989).
(2) D. I. Gittins, F. Caruso, *J. Phys. Chem. B* 105, 6846-6852 (2001).
(3) C. A. Mirkin, R. L. Letsinger, R. C. Mucic, J. J. Storhoff, *Nature* 382, 607-609 (Aug. 15, 1996).
(4) Letsinger, R. L.; Elghanian, R.; Viswanadham, G.; Mirkin, C. A. *Bioconjugate Chemistry* 2000, 11, 289-291.
(5) Storhoff, J. J.; Elghanian, R.; Mucic, R. C.; Mirkin, C. A.; Letsinger, R. L. *Journal of the American Chemical Society* 1998, 120, 1959-1964.
(6) Grabar, K. C.; Freeman, R. G.; Hommer, M. B.; Natan, M. J. *Analytical Chemistry* 1995, 67, 735-743.
(7) *Oligonucleotides and Analogues*, 1st ed.; Eckstein, F., Ed.; Oxford University Press: New York, 1991.

What we claim:

1. A nanoparticle having a plurality of polyanionic polymer conjugates attached thereto, said polyanionic polymer conjugates having the formula L—O—[$PO_2$—O-Z-O]$_n$—$PO_2$—O—X wherein n ranges from 1 to 200; L represents a moiety comprising a functional group for attaching the polyanion polymer to a nanoparticle surface; Z represents a bridging group, and X represents Q, X' or -Q-X', wherein Q represents a functional group comprising a carboxylic acid or an amino group for attaching a recognition probe to the polyanion polymer, and X' represents a recognition probe.

2. The nanoparticle of claim 1, wherein the polyanionic polymer conjugate further comprises a detection label bound thereto.

3. The nanoparticle of claim 2, wherein the detection label comprises a chromophore, a fluorescent label, a UV label, a radioisotope, a Raman label or a SERS (surface enhanced raman spectroscopy) label, or an enzyme.

4. The nanoparticle of claim 1, wherein the recognition probe comprises a protein, a peptide, a nucleic acid, a peptide nucleic acid, a linked nucleic acid, a nucleoside triphosphate, a carbohydrate, a lipid, a lipid bound protein, an aptamer, a virus, a cell fragment, or a whole cell.

5. The nanoparticle of claim 4, wherein the lipid bound protein comprises a G-protein coupled receptor.

6. The nanoparticle of claim 1, wherein the recognition probe comprises an antibody, an antigen, a receptor, or a ligand.

7. The nanoparticle of claim 1 wherein L comprises an alkanethiol containing group, a phosphorothioate containing group, a substituted alkylsiloxane containing, a polythiol containing group, or a cyclic disulfide containing group.

8. The nanoparticle of claim 1 wherein Z comprises a polymer, —$C_1$-$C_{10}$-alkyl-, —COO—, —$CHR_2(CH_2)_v$COO—, —OCO—$R^1N(CH_2)_{v-NR}{}^1$—, —OC($CH_2$)$_v$—, —($CH_2$)$_v$—, —O—($CH_2$)$_v$—O—, —RN—($CH_2$)$_v$—, -continued v is 0-30 and $R^1$ is H or is $G(CH_2)_v$, wherein G is $—CH_3$, $—CHCH_3$, $—COOH$, $—CO_2(CH_2)_vCH_3$, $—OH$, or $—CH_2OH$.

9. A kit for detecting the presence or absence of a target analyte in a sample comprising:

(a) nanoparticles having polyanionic polymer conjugates bound thereto, wherein the polyanion polymers have the formula:

wherein n ranges from 1 to 200; L represents a moiety comprising a functional group for attaching the polyanion polymer to a nanoparticle surface; Z represents a bridging group, and X represents Q, X' or -Q-X', wherein Q represents a functional group comprising a carboxylic acid or an amino group for attaching a recognition probe to the polyanion polymer, and X' represents a recognition probe; and (b) an optional substrate for observing a detectable change.

10. The kit of claim 9, wherein the polyanionic polymer conjugate further comprises a detection label bound thereto.

11. The kit of claim 10, wherein the detection label comprises a chromophore, a fluorescent label, a UV label, a radioisotope, a Raman label or a SERS (surface enhanced raman spectroscopy) label, or an enzyme.

12. The kit of claim 9, wherein the probe comprises a protein, a peptide, a nucleic acid, a peptide nucleic acid, a linked nucleic acid, a nucleoside triphosphate, a carbohydrate, a lipid, a lipid bound protein, an aptamer, a virus, a cell fragment, or a whole cell.

13. The kit of claim 12, wherein the lipid bound protein comprises a G-protein coupled receptor.

14. The kit of claim 9, wherein the probe comprises an antibody, an antigen, a receptor, or a ligand.

15. The kit of claim 9 wherein the substrate is a transparent substrate or an opaque white substrate.

* * * * *